United States Patent
Stangelmayer et al.

(10) Patent No.: US 11,313,703 B2
(45) Date of Patent: Apr. 26, 2022

(54) SENSOR DEVICE AND MEASURING METHOD COMPRISING PLURAL LIGHT GUIDES WITH EACH SECOND END DISPOSED AT A DEFINED PERPENDICULAR DISTANCE TO THE FIRST END ON A CARRIER

(71) Applicant: PreSens Precision Sensing GmbH, Regensburg (DE)

(72) Inventors: Achim Stangelmayer, Neuburg an der Donau (DE); Gregor Liebsch, Obertraubling (DE); Gernot Thomas John, Koefering (DE); Robert J. Meier, Nittendorf (DE); Daniela Obermaier, Plattling (DE)

(73) Assignee: PRESENS PRECISION SENSING GMBH, Regensburg (DE)

( * ) Notice: Subject to any disclaimer, the term of this patent is extended or adjusted under 35 U.S.C. 154(b) by 343 days.

(21) Appl. No.: 16/689,393

(22) Filed: Nov. 20, 2019

(65) Prior Publication Data

US 2020/0173817 A1 Jun. 4, 2020

(30) Foreign Application Priority Data

Nov. 29, 2018 (DE) ..................... 10 2018 130 299.1

(51) Int. Cl.
| | | |
|---|---|---|
| *G01N 21/25* | (2006.01) | |
| *G01D 5/353* | (2006.01) | |
| *G01N 21/64* | (2006.01) | |

(52) U.S. Cl.
CPC ......... *G01D 5/3537* (2013.01); *G01N 21/255* (2013.01); *G01N 21/64* (2013.01); *G01N 2201/088* (2013.01)

(58) Field of Classification Search
CPC ....... G01N 21/0303; G01N 2021/0325; G01N 2021/0346; G01N 21/17; G01N 21/255;
(Continued)

(56) References Cited

U.S. PATENT DOCUMENTS

| | | |
|---|---|---|
| 6,620,612 B1 | 9/2003 | Bertling |
| 9,719,138 B2 * | 8/2017 | Zhong ................ G01N 21/6454 |
| 2018/0292393 A1 | 10/2018 | Neilson et al. |

FOREIGN PATENT DOCUMENTS

| | | |
|---|---|---|
| DE | 10227962 A1 | 1/2004 |
| DE | 102011055272 A1 | 5/2013 |

(Continued)

OTHER PUBLICATIONS

Weyand et al., Noninvasive Oxygen Monitoring in Three-Dimensional Tissue Cultures Under Static and Dynamic Culture Conditions, BioResearch, Open Access, 2015, pp. 266-277, vol. 4.1.
(Continued)

*Primary Examiner* — Que Tan Le
(74) *Attorney, Agent, or Firm* — Patentbar International PC

(57) ABSTRACT

In a sensor device, a plurality of light guides having a respective first end and a respective second end are arranged on a common carrier, with the first end of each light guide of the plurality of light guides at a respective defined position on the carrier. At each of the second ends of the light guides there is provided at least one sensor element which exhibits an optical behavior dependent on an analyte. The second ends are at defined perpendicular distances to the carrier. At least two of the second ends differ with respect to the defined perpendicular distances.

14 Claims, 5 Drawing Sheets

(58) Field of Classification Search
CPC .... G01N 21/31; G01N 21/41; G01N 21/6408;
G01N 21/6428; G01N 21/6486
USPC .......... 250/221, 239, 227.11, 227.24, 227.25
See application file for complete search history.

(56) References Cited

FOREIGN PATENT DOCUMENTS

| | | |
|---|---|---|
| DE | 102013109010 A1 | 2/2015 |
| EP | 0425587 B1 | 6/1994 |
| JP | H10-281994 A | 10/1998 |
| WO | 2001/059432 A2 | 8/2001 |
| WO | 2003/064990 A2 | 8/2003 |
| WO | 2019/008461 A1 | 1/2019 |

OTHER PUBLICATIONS

Laser μFAB Microfabrication Workstation, Data Sheet.
Fischer et al., The multi fiber optode (MuFO): A novel system for simultaneous analysis of multiple fiber optic oxygen sensors, Sensors and Actuators B: Chemical, 2012, pp. 354-359, v. 168.
Liebsch, Gregor, The Dissertation, Time-Resolved Luminescence Lifetime Imaging with Optical Chemical Sensors, Set-up, controlling, Concepts and Applications, University of Regensburg, Oct. 2000.

\* cited by examiner

SENSOR DEVICE AND MEASURING METHOD COMPRISING PLURAL LIGHT GUIDES WITH EACH SECOND END DISPOSED AT A DEFINED PERPENDICULAR DISTANCE TO THE FIRST END ON A CARRIER

RELATED APPLICATIONS

This application claims priority to German Patent Application DE 10 2018 130 299.1, filed Nov. 29, 2018, which is incorporated herein by reference in its entirety.

FIELD OF THE INVENTION

The invention relates to a sensor device with sensor elements which show an optical behavior dependent on an analyte, as well as to a corresponding measuring method.

BACKGROUND OF THE INVENTION

The optical monitoring of biological structures such as two-dimensional or three-dimensional cell cultures is currently carried out using oxygen- and pH-sensitive dyes in cell culture media (Weyand et al., Biores. Open Access 4, 266-277 (2015)). In some applications this cannot be done without disturbances, as some cells do not tolerate this indication and the interaction with the dye significantly distorts the result.

In addition, there are numerous systems for the measurement of marker molecules, proteins, nutrients and metabolites outside the culture. These require sampling and elaborate sample preparation as well as sophisticated analytical techniques such as capillary electrophoresis, mass spectroscopy or enzymatic assay systems. Sampling removes part of the medium, which can mean the end of cultivation, especially with small culture volumes in 96-well plate format.

Some parameters can be observed directly in the cell medium. Phenol red, for example, is a component of most culture media (approx. 15 mg/L) and serves as a pH indicator as well as an indicator of bacterial contamination.

Fluorescent proteins such as GFP, which are expressed in the cell, provide another way of carrying out investigations in living cells. However, this requires genetic manipulation of the cells, which is not permitted in the case of subsequent medical application of the cell clusters.

In contrast to alternative methods such as fluorescence microscopy, the invention should be able to determine the parameters directly in the process without sample preparation. It should also be possible to use the sample after observation without any processing steps. This is the only way to optimize the process, as this is the only way to ensure that cultivation is not influenced during the measurement.

The advantages of the invention lie in the simplified, miniaturized measuring methodology and its simple application and the possibility of working in complex samples under sterile conditions. The invention determines several (bio)chemical parameters in real-time and with spatial resolution without contamination. In particular, the possibility of determining dissolved $CO_2$ concentrations in biological samples provides a new perspective for studying and optimizing cell growth and metabolism.

The overriding interest in solving the problem lies in the constantly increasing demand for three-dimensional cell cultures, especially in research and development as well as in the field of regenerative medicine. Unfortunately, the extremely high demands on the vitality of the cells of >5% in spheroids, e.g. for use in the transplantation of chondrocytes (cartilage cells), lead to corresponding failure rates in the cultivation of the cells. This in turn leads to immense costs for cell-based therapeutics, caused by the many parallel cultivation approaches. This failure rate could be reduced by up to 20% by targeted cultivation monitoring.

Three-dimensional signal acquisition makes it possible to differentiate between cells at different positions in the cell compound. Since the measurement does not require sampling and the sensor elements and light guides are designed in such a way that they do not inhibit cell growth, further cultivation of the culture is also possible after the measurement without any problems.

Overall, the concept enables, for example, early detection of nutrient deficiencies or contaminations before they become visible during a morphological microscopic revision of the cells, thus enabling timely intervention.

US patent application US 2018/0292393 A1 relates to a device and associated method for the measurement of properties of biological samples. A lid for a microtiter plate is provided with protrusions at the end of which sensors are mounted. When the lid is placed on the microtiter plate, a protrusion dips into each well of the microtiter plate. The sensors are read through the bottom of the microtiter plate. With such an arrangement, maintaining an exact distance to the bottom of the respective well is problematic. The lid is placed as a unit on the microtiter plate; in addition to tolerances in the production of the protrusions, there are also tolerances in the formation of the individual wells, which cannot be compensated for by spacers for the lid due to their individual nature. With this type of lid, one is limited to microtiter plates of a suitable size as sample carriers. It is not possible to record the distribution of the analyte at defined positions.

It is also known to attach sensors to the ends of individual light guides and to position these ends of the light guides in a sample. This results in difficulties with the exact positioning of the sensors in the sample and also with the passing of the individual light guides through the sample. A bundled passing of several such light guides is also possible, which however results in a restriction regarding the positioning of the light guides in relation to each other in the sample, see the article "The multi fiber optode (MuFO): A novel system for simultaneous analysis of multiple fiber optic oxygen sensors" by J. P. Fischer et al., in Sensors and Actuators B: Chemical, Volume 168, pages 354-359, 2012.

It is also known to address the individual wells of a microtiter plate and the sensors located therein via individual light guides, and to bundle the opposite ends of the light guides onto a smaller surface in order to adapt to the format of detector chips, see the dissertation of Gregor Liebsch, "Time-Resolved Luminescence Lifetime Imaging with Optical Chemical Sensors", University of Regensburg, 2000. Here, too, it is not possible to record the distribution of the analyte at defined positions in the sample.

The international patent application PCT/IB2018/054575 discloses a sensor foil inclined against the horizontal in a sample volume, so that values of the analyte can be recorded at different distances, e.g. from a bottom of the sample container. The various holding devices for the inclined sensor foil represent a noticeable intervention in the sample volume.

SUMMARY OF THE INVENTION

It is an object of the invention to provide a sensor device with which an analyte in a sample can be measured at defined positions within the sample volume, whereby the required interventions in the sample volume are to be reduced. A corresponding measurement procedure also is to be specified.

The object with regard to the sensor device is achieved by a sensor device according to claim 1. Claims 10 and 11 relate to manufacturing methods for the sensor device. Claims 12-14 relate to corresponding measuring methods.

The dependent claims relate to respective advantageous embodiments.

The sensor device according to the invention comprises a plurality of light guides. Each light guide has a first end and a second end. The sensor device comprises a plurality of sensor elements. Each sensor element has an optical behavior that depends on at least one analyte. Each sensor element of the plurality of sensor elements is located on a second end of a light guide of the plurality of light guides. According to the invention, the first ends of the light guides are arranged on a carrier at a respective defined position and the second end of each light guide of the plurality of light guides is at a defined perpendicular distance to the carrier. In this way, an analyte can be measured at defined distances from the carrier; in particular, one is not limited to attaching sensor elements to walls of a sample container. The defined arrangement of the light guides on the carrier also eliminates the difficulty of arranging individual light guides in a defined manner in a sample and of fixing them in their respective positions. The carrier with the light guides is intended to be inserted into a sample container unless the carrier itself already forms part of a sample container.

The light guides are sufficiently stable of shape in the sense that the light guides are not significantly deformed either under their own weight or by the effect of a sample in which at least one analyte is to be measured. A significant deformation here is to be understood as a deformation in which the position of the second end of the light guide relative to the carrier changes to an extent which results in an unacceptable corruption of the measurement results, depending on the specific measurement task. For example, the change in position of a second end of a light guide relative to the carrier should not exceed one diameter of the respective light guide; smaller changes in position are of course preferred.

At the second end of a light guide several sensor elements may be arranged, which may be sensitive to different analytes, i.e. each of the sensor elements shows an optical behavior which depends on a respective analyte. The sensor elements may be polymer films in which a sensor substance, such as an indicator dye, is embedded. In this case, it is the sensor substance that shows the optical behavior that depends on the analyte. However, the invention is not limited to this type of sensor element. The sensor elements may also have protective layers that are permeable to an analyte but keep other substances, such as water, away from the sensor substance. The sensor elements may, for example, be generated by one or more coating processes directly at the second ends of the light guides. A different attachment of the sensor elements at the second ends of the light guides is of course also conceivable.

The optical behavior, for example, may be a change in color, a change in reflectivity, or a luminescent phenomenon. Luminescence includes phosphorescence and fluorescence. In luminescence, a relaxation time of the luminescence may depend on the analyte to be measured. Such different types of optical behavior and their exploitation for the measurement of an analyte are known to the skilled person.

According to the invention, the defined perpendicular distances of the second ends to the carrier differ for at least two light guides of the plurality of light guides. In this way, an analyte can be measured at defined different distances from the carrier and, so to speak, results can be obtained on the three-dimensional distribution of the analyte, for example on concentration gradients of an analyte in the direction perpendicular to the carrier.

Generally speaking, concentration gradients can also be measured by moving a sensor, such as a microsensor on a micromanipulator, through a liquid sample and taking measurements when the sensor is at defined positions within the sample. However, the movement of a sensor, even a microsensor, through the sample can cause local mixing of the sample, so that any concentration gradients in the vicinity of the sensor are smeared. When using a sensor device according to the invention, such a local mixing of the sample does not occur because the sensor elements do not have to be moved through the sample; nevertheless, a concentration gradient can be determined.

Sensor devices in which the second ends of all light guides of the plurality of light guides are at the same perpendicular distance to the carrier, apart from any manufacturing tolerances, are also conceivable.

In one embodiment, each light guide follows a predetermined path from its first end to its second end. In this way, a sensor device can be adapted to the geometric conditions of the sample, such as a cell culture. In the simplest case, the light guides run straight and perpendicular to the carrier, more precisely perpendicular to the surface of the carrier on which they are arranged. However, the light guides may also be inclined against this surface or have a curved form. It is always important that the position of the second end of the light guide, and thus of the one or more sensor elements at this second end, is defined relative to the carrier, especially because it is predetermined by the manufacture of the sensor device.

In one embodiment, a group of light guides from the plurality of light guides agree with regard to the sensor elements arranged at their respective second ends, i.e. all light guides in the group have sensor elements of the same type at their second ends, which in particular are sensitive to the same analyte. The group may, but does not have to, include all light guides of the sensor device. For each light guide in the group, the second end is at a different perpendicular distance to the carrier. In this way, an analyte can be measured at different distances perpendicular to the carrier. For example, the distance of the second end of a first light guide of the group perpendicular to the carrier could be 100 µm, the distance of the second end of a second light guide of the group perpendicular to the carrier could be 50 µm, the distance of the second end of a third light guide of the group perpendicular to the carrier could be 10 µm. Neither the mentioned distances nor the number of light guides of a group, however, represent restrictions for the invention.

The carrier is preferably transparent, in particular the carrier may be made of glass or a polymer. In the case of a transparent carrier, light can simply be coupled into the light guides through the carrier and light can also simply be coupled out of the light guides through the carrier.

In an advantageous embodiment, the light guides and carrier are made of the same transparent material and are materially bonded together. In particular, light guides and carrier may form a single one-piece element.

A support for a cell culture, such as a cell crown, may be provided on the carrier. The support may be integral with the carrier, or the carrier may have attachment areas for the support.

In one embodiment, one or more areas for interaction with a positioning device for the sensor device are formed on the carrier. With the positioning device, the sensor device can be placed reliably and with sufficient positioning accuracy in a sample container. For example, it would be conceivable to glue the carrier of the sensor device to a wall of the sample container, whereby the carrier is positioned by the positioning device. For example, the positioning device may hold the carrier by vacuum or the positioning device may be a gripper gripping the carrier at one or more areas intended to interact with the gripper. Other types of positioning devices are also possible. By providing certain areas for interaction with a positioning device, the danger of light guides being damaged or changed in their path by the positioning device is reduced.

In another embodiment, the carrier is formed by at least one wall of a sample container. This means that in this embodiment, the carrier with the light guides is not a separate component that can be inserted into a sample container, but the light guides are formed directly on the wall of a sample container.

The light guides can be formed by 3D printing. In addition, the carrier can also be manufactured by 3D printing. In particular, a carrier with light guides can be produced by 3D printing as a single element. This process is particularly suitable if the carrier and the light guides are made of a polymer.

In an alternative manufacturing process for a sensor device described above, the light guides are manufactured by material ablation and/or material restructuring using laser radiation. This process is particularly suitable if the carrier and light guides are made of glass. A femtosecond laser can be used, for example, in a "Laser μFAB Microfabrication Workstation" from Newport.

For example, a method to measure at least one analyte in a sample is performed as follows: At least one sensor device of the type described above is placed in a sample container. Before or after this placement, the sample is filled into the sample container. Excitation light is then coupled into at least a subset of the light guides of the sensor device, so not all light guides of the sensor device need to be used for each measurement. The excitation light is suitable to excite the optical behavior, dependent on the analyte to be measured, of at least one sensor element which is arranged at the second end of a light guide of the subset of the light guides. The response of the sensor element is light, corresponding to the optical behavior of the sensor element. This light of the response of the at least one sensor element is guided through the subset of the light guides and detected by at least one detector. The output signal of the at least one detector is evaluated to measure the at least one analyte. In a special variant of the method, a respective sensor device is arranged in each of a plurality of wells of a microtiter plate.

One variant of the method uses a sensor device according to the invention in which the carrier is a wall of a sample container. Here the sample container is filled with the sample. Excitation light is then coupled into at least a subset of the light guides of the sensor device; thus not all light guides of the sensor device need to be used for each measurement. The excitation light is suitable to excite the optical behavior, dependent on the analyte to be measured, of at least one sensor element, which is arranged at the second end of a light guide of the subset of the light guides. The response of the sensor element is light, corresponding to the optical behavior of the sensor element. This light of the response of the at least one sensor element is guided through the subset of the light guides and detected by at least one detector. The output signal of the at least one detector is evaluated to measure the at least one analyte.

In the measuring methods, the detection by a detector can be advantageously carried out by taking an image of a transparent carrier from the side of the carrier facing away from the light guides. Due to the defined arrangement of the first ends of the light guides on the carrier, each light guide can be identified in the image. Since the position of the second end of each light guide is also known, it is possible to determine in the recorded image from which location in the sample the respective signals originate.

For the optical excitation of a sensor substance and for the evaluation of the optical response of the sensor substance, the skilled person is familiar with numerous methods. Examples can be found, for example, in the German patent applications DE 10 2011 055 272 A1 and DE 10 2013 109 010 A1, as well as in prior art documents cited therein. Such methods can also be used if the sensor device according to the invention is used. The skilled person is also familiar with a large number of sensor substances and their suitability for measuring the respective analytes.

The measurement of an analyte, i.e. a substance to be detected, means that the concentration or partial pressure of the analyte in the sample is determined up to error limits customary in the field, or that it is determined if concentration or partial pressure of the analyte are within a certain range. This range can have an upper limit and a lower limit, or only an upper limit or only a lower limit.

The sample may be a cell culture medium, but the invention is not limited thereto. The sensor device according to the invention and the measurement methods according to the invention can be generally used for liquid samples, but also for gaseous samples; they can also be used for samples in the form of granular matter.

BRIEF DESCRIPTION OF THE DRAWINGS

In the following, the invention and its advantages are explained in more detail using the accompanying figures.

The figures are only examples of how the invention may be configured and serve to explain and illustrate certain details of possible embodiments. Under no circumstances should the figures and their accompanying description be construed as a limitation of the invention to the embodiments depicted in the figures.

DETAILED DESCRIPTION OF THE PREFERRED EMBODIMENTS

Figure 1:
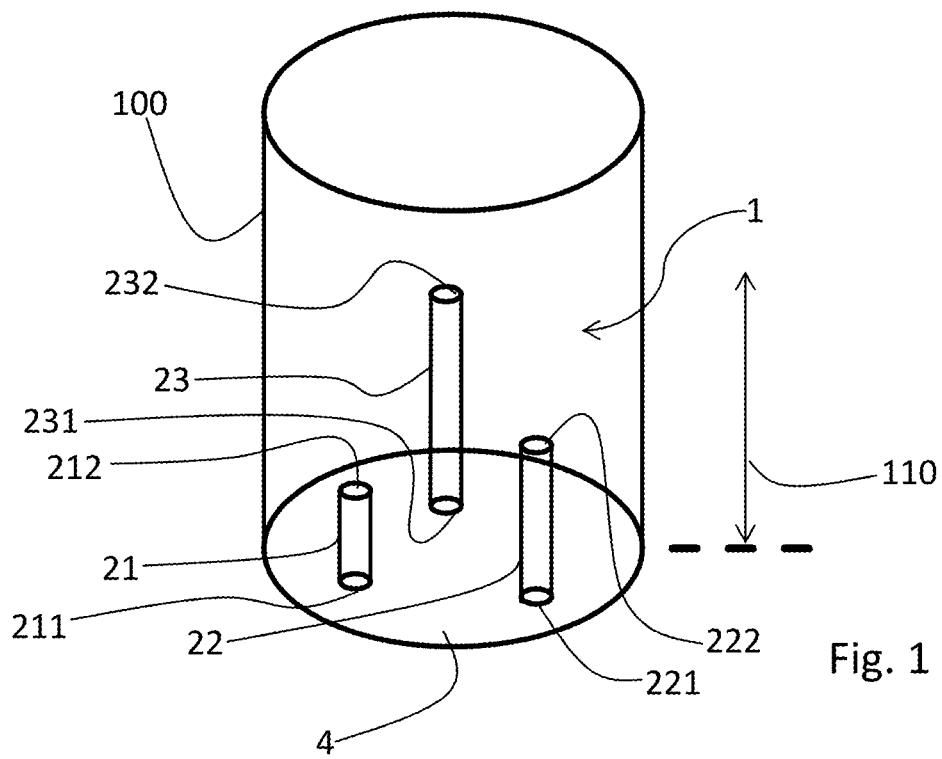
FIG. 1 shows a schematic perspective view of a sensor device according to the invention in a sample container.

FIG. 1 shows a schematic perspective view of a sensor device 1 according to the invention in a sample container 100. In the embodiment shown, three light guides 21, 22, 23 are arranged on a carrier 4 of the sensor device 1. A respective first end, 211, 221, 231, of the light guides 21, 22, 23 is arranged at a defined position on the carrier 4. A respective second end, 212, 222, 232, of the light guides 21, 22, 23 is located at a defined perpendicular distance 110 to the carrier 4. In the embodiment shown, this defined distance 110 is different for each of the light guides 21, 22, 23. At the second end 212, 222, 232 of each light guide 21, 22, 23 at least one sensor element is provided (not shown). Each sensor element has an optical behavior that depends on at least one analyte.

Figure 2:
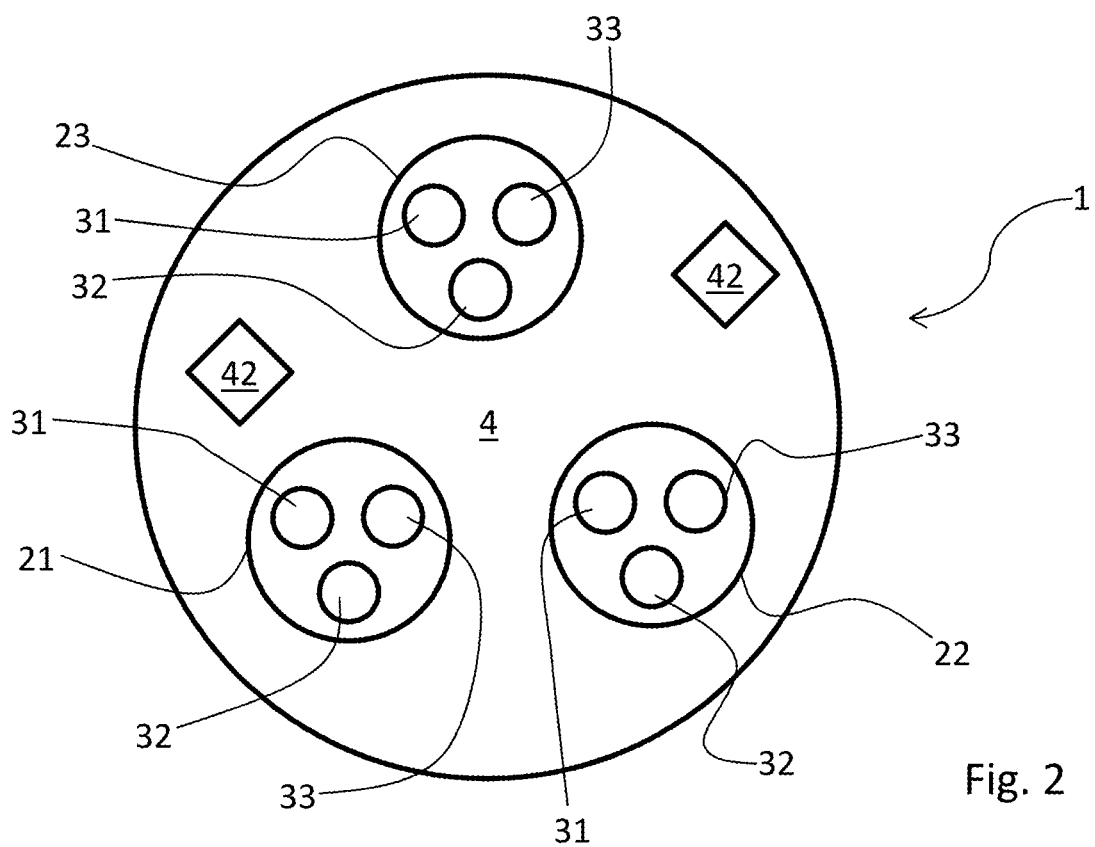
FIG. 2 shows a schematic top view of a sensor device according to the invention.

FIG. 2 shows a schematic top view of a sensor device 1 according to the invention. The carrier 4 and the light guides 21, 22, 23 are shown. Three sensor elements 31, 32, 33 are arranged at each of the second ends of the light guides 21, 22, 23 in the embodiment shown, and the sensor elements 31, 32, 33 are identical for all three light guides 21, 22, 23. Each of the sensor elements 31, 32, 33 is sensitive to a different analyte, i.e. shows a respective optical behavior that depends on a respectively different analyte. For example, sensor element 31 may be pH sensitive, sensor element 32 may be oxygen sensitive and sensor element 33 may be carbon dioxide sensitive. In general, an inventive sensor device 1 may include more than three light guides. At least one sensor element is arranged at the second end of each light guide, in the arrangement shown in FIG. 2 there are three sensor elements per second end, which does not constitute a limitation of the invention. Similarly, the circular cross-section of the carrier, light guides and sensor elements does not restrict the invention. It is also conceivable that at the second end of a light guide one or more elements are provided for referencing or calibration. Also shown here are two areas 42 which are intended to interact with a positioning device.

Figure 3:
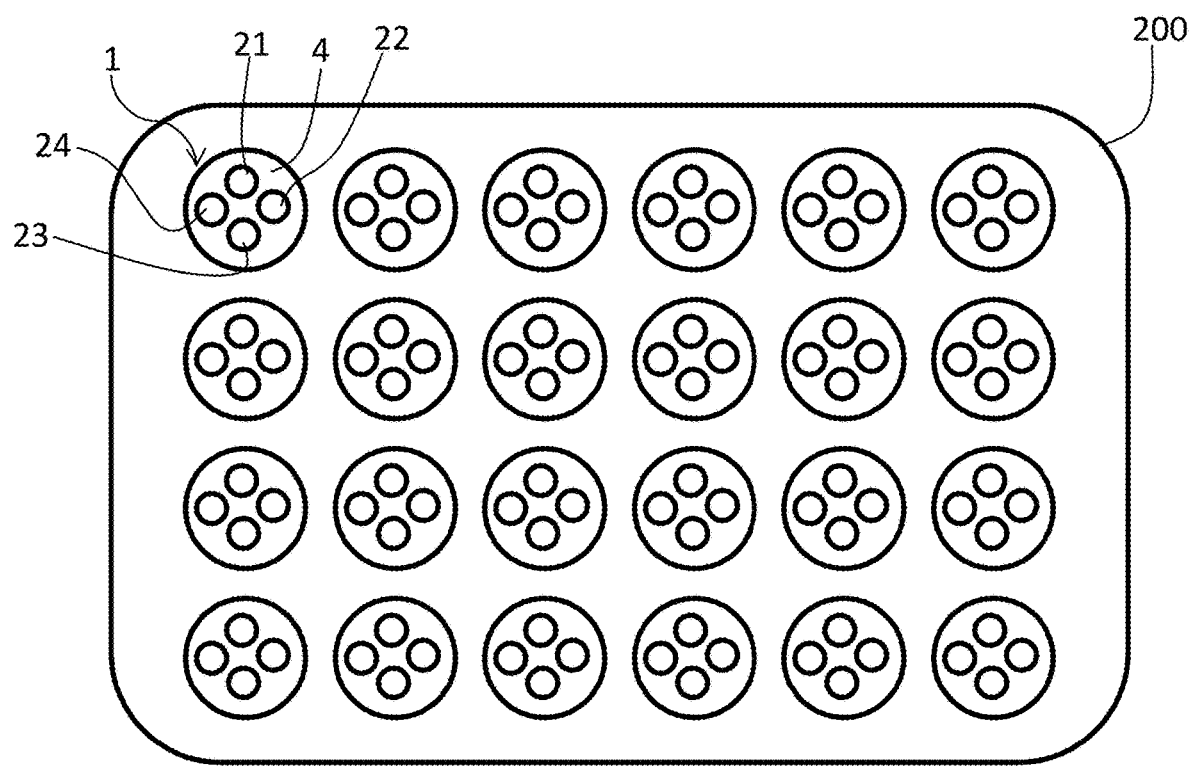
FIG. 3 shows a schematic view of a plurality of sensor devices according to the invention when used in a microtiter plate.

FIG. 3 shows a plurality of sensor devices 1 according to the invention, each of the sensor devices 1 being inserted into a well of a microtiter plate 200. Each of the sensor devices 1 comprises four light guides 21, 22, 23, 24. On each of the light guides 21, 22, 23, 24 one or more sensor elements may be arranged at its respective second end, as discussed for example for FIG. 2.

Figure 4:
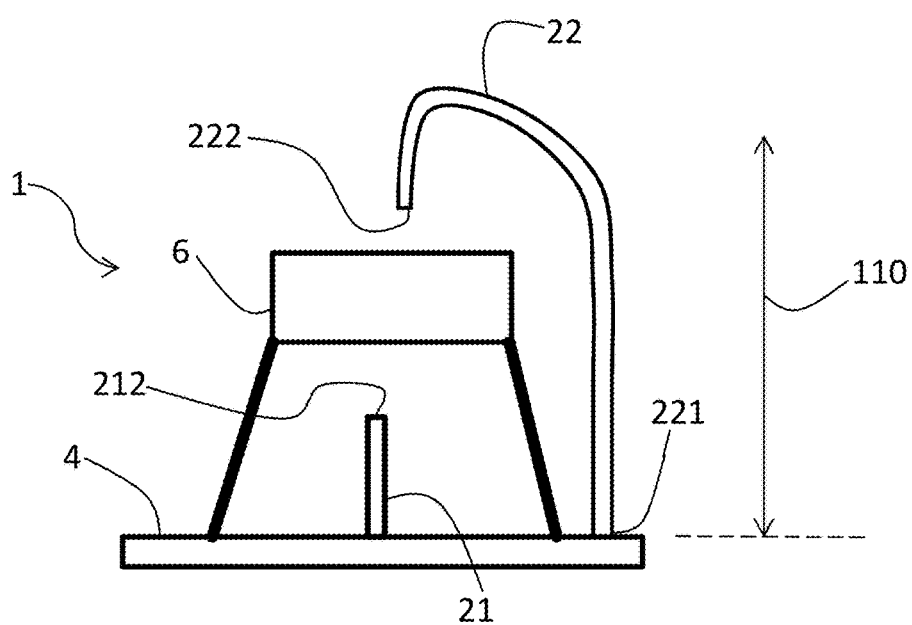
FIG. 4 schematically shows an example of the use of a sensor device according to the invention together with a cell crown.

FIG. 4 schematically shows a sensor device 1 according to the invention in connection with a cell crown 6, which is intended as support for a cell culture. The cell crown 6 is mounted on the carrier 4 of the sensor device 1. Sensor device 1 here comprises two light guides 21, 22, at the second ends 212 and 222 of which at least one respective sensor element (not shown) is arranged. The two second ends 212, 222 are located at different perpendicular distances 110 to the carrier 4. In the embodiment shown, the light guide 21 runs straight and perpendicular to the carrier 4. The light guide 22 has a curved shape. Thus, although the first end 221 of the light guide 22 is arranged on the carrier 4 to the side of the cell crown 6, the second end 222 of the light guide 22 can be positioned above the cell crown 6, and thus the one or more sensor elements at the second end 222 can measure one or more analytes above the cell crown 6.

Figure 5:
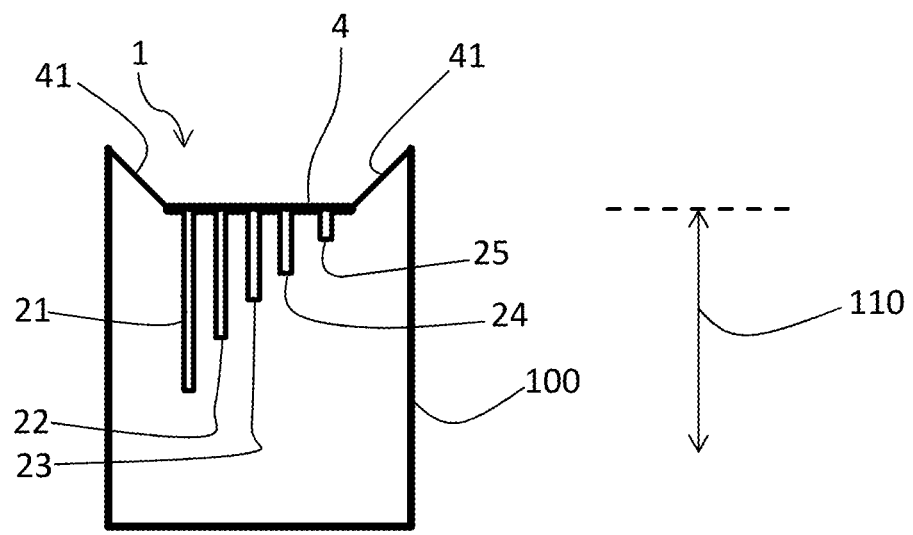
FIG. 5 schematically shows another example of the use of a sensor device according to the invention in a sample container.

FIG. 5 shows a sample container 100 in which a sensor device 1 according to the invention is mounted. The carrier 4 of the sensor device 1 is suspended from the upper edge of the sample container 100 via retaining elements 41. In the example shown, the light guides 21, 22, 23, 24, 25 of sensor device 1 extend downwards. The second ends of the light guides 21, 22, 23, 24, 25 are at different defined perpendicular distances 110 to the carrier 4. The retaining elements 41 may be configured such that the sample container 100 remains open at the top. Alternatively, retaining elements 41 and carrier 4 together may form a lid which closes the sample container 100.

Figure 6:
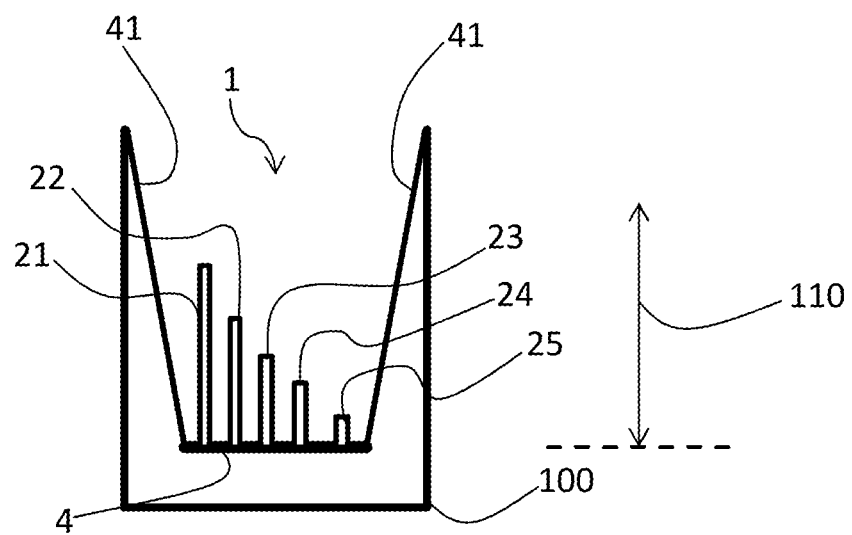
FIG. 6 schematically shows another example of the use of a sensor device according to the invention in a sample container.

FIG. 6 shows an arrangement which is largely analogous to that shown in FIG. 5. In contrast to the arrangement shown in FIG. 5, the light guides 21, 22, 23, 24, 25 extend upwards to the opening of the sample container 100.

Figure 7:
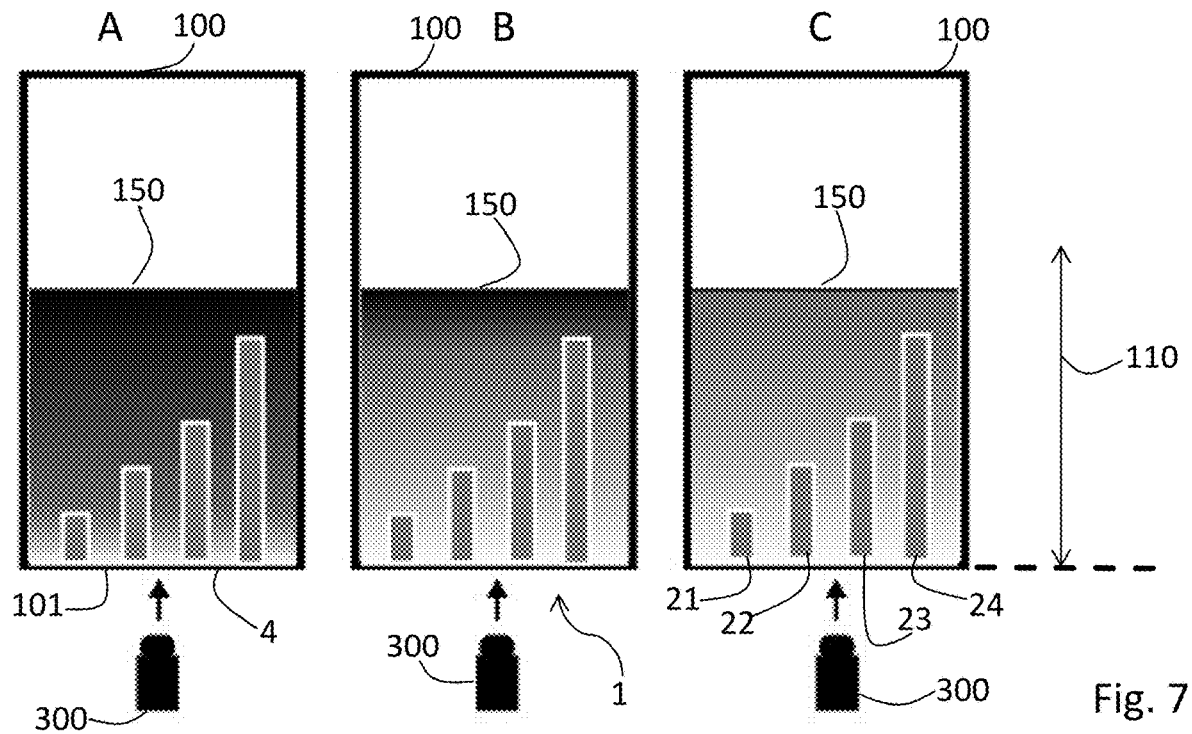
FIG. 7 schematically shows a respective sensor device according to the invention in sample containers with different oxygen concentration profile.

FIG. 7 shows a sample container 100, in which there is a sample 150, as well as a sensor device 1 according to the invention. In the embodiment shown the carrier 4 of the sensor device 1 is a wall 101, more precisely the bottom, of the sample container 100, and the sensor device 1 comprises four light guides 21, 22, 23, 24. For the example shown it is assumed that at each of the second ends of the light guides 21, 22, 23, 24 an oxygen-sensitive sensor element is arranged. Also shown is a camera 300 for taking an image of sensor device 1 through the transparent bottom of sample container 100, i.e. here through the carrier 4 of sensor device 1. Light sources for excitation of the optical behavior of the respective sensor elements of sensor device 1 may be provided on the camera 300 or elsewhere in the setup if required. Other optical elements may also be provided to guide the excitation light and response of the sensor elements. These optical elements are not shown here because they are irrelevant to the invention and must be selected by the skilled person in a known manner depending on the specific setup.

The setup described above is shown in FIG. 7 in three situations A, B, C, which differ in the dependence of the oxygen concentration on the perpendicular distance 110 to the carrier 4. Areas of different oxygen concentration are indicated in the figure by different grey tones. Darker grey tones mean a higher oxygen concentration.

Figure 8:
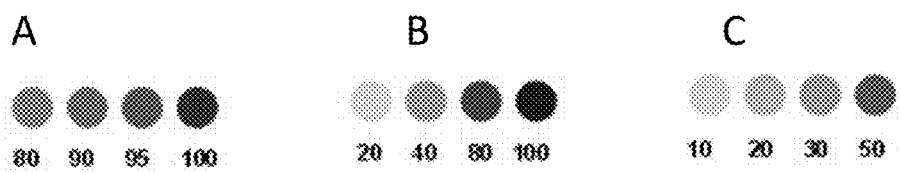
FIG. 8 schematically shows an image captured in each case for the arrangement from FIG. 7.

FIG. 8 with reference to FIG. 7 schematically shows the images recorded by the camera 300 in situations A, B and C, i.e. the optical response of the sensor elements at the second ends of the light guides 21, 22, 23, 24, transmitted via the light guides 21, 22, 23, 24 and through the carrier 4, and captured by a detector in the camera 300. The circles shown, which correspond to the respective light guides, are represented in different grey tones according to the respective oxygen concentration. The numbers below the circles are percentages indicating the respective oxygen concentration relative to the oxygen concentration in the atmosphere.

Figure 9:
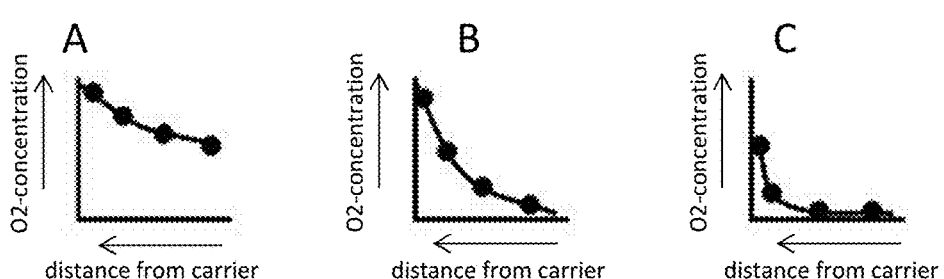
FIG. 9 shows schematic diagrams showing the profile of the oxygen concentration as a function of position.

FIG. 9 shows with reference to FIG. 7 three diagrams, one for each of the situations A, B, C, which schematically show the profile of the oxygen concentration as a function of the distance from the carrier. The four points on the curve correspond to the value of the oxygen concentration at the location of one of the second ends of the light guides 21, 22, 23, 24.

Figure 10:
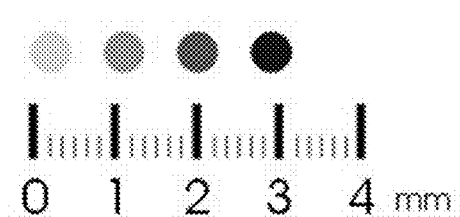
FIG. 10 shows a length scale associated with FIGS. 7 to 9.

FIG. 10, with reference to FIG. 7 and FIG. 8, and for the example of the images of the circles for situation B, shows the dependence on distance of the oxygen concentration on the basis of a scale, which indicates the distance of the second ends of the respective light guides 21, 22, 23, 24 from the carrier 4.

Figure 11:
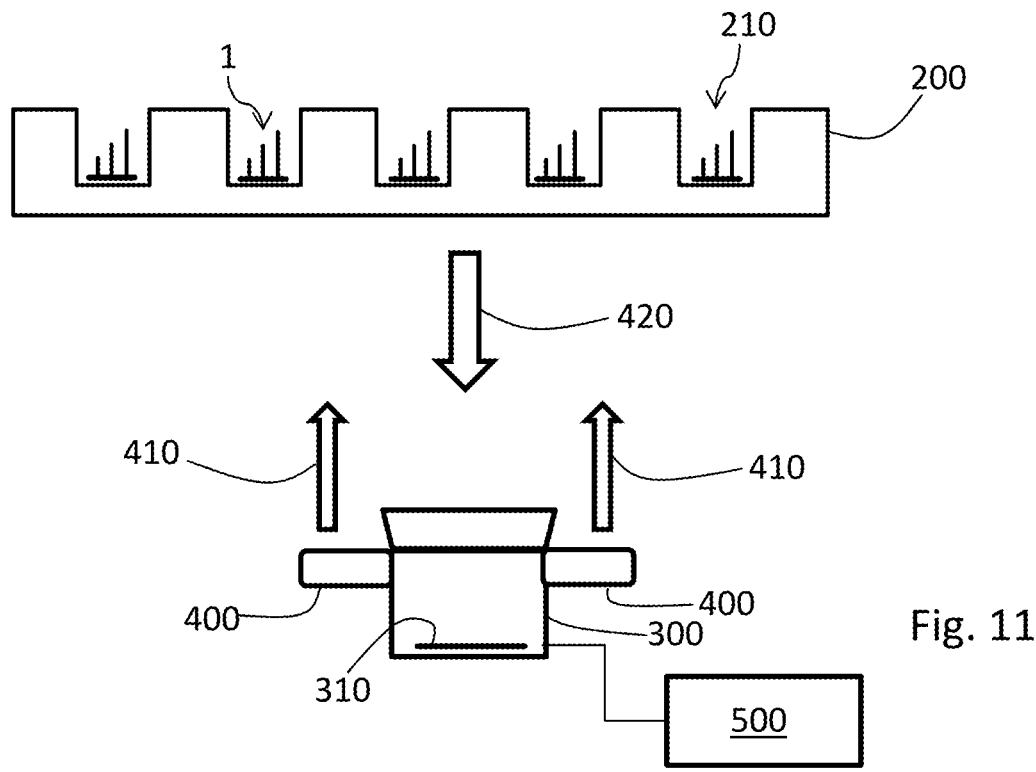
FIG. 11 shows a microtiter plate with several sensor devices according to the invention together with a camera.

FIG. 11 schematically shows a transparent microtiter plate 200, in the wells 210 of which a respective sensor device 1 according to the invention has been inserted. Of the sensor device 1 the transparent carrier and three light guides are shown. A ring light 400 is arranged on a camera 300 with detector 310. The ring light 400 is intended to emit excitation light 410 in the direction of the plurality of sensor devices 1 in the microtiter plate 200. Light 420 of an optical response of the sensor elements of the sensor devices 1 is imaged by the camera 300 onto the detector 310. A control unit 500 is provided to control the ring light 400 and the camera 300. In the example shown, the control unit 500 also evaluates the output signals of the detector 310 in order to determine the concentration or partial pressure of at least one analyte from these output signals. To perform its tasks, the control unit 500, for example, has one or more microprocessors and memory units. The memory units contain program instructions for performing measurement protocols and evaluation procedures, as well as additional data required for these purposes, such as calibration data.

A camera and a ring light or a different source of illumination may of course also be used if the sample container is not a microtiter plate but is configured differently; non-restrictive examples for other sample containers would be beakers, Erlenmeyer flasks, bottles.

Figure 12:
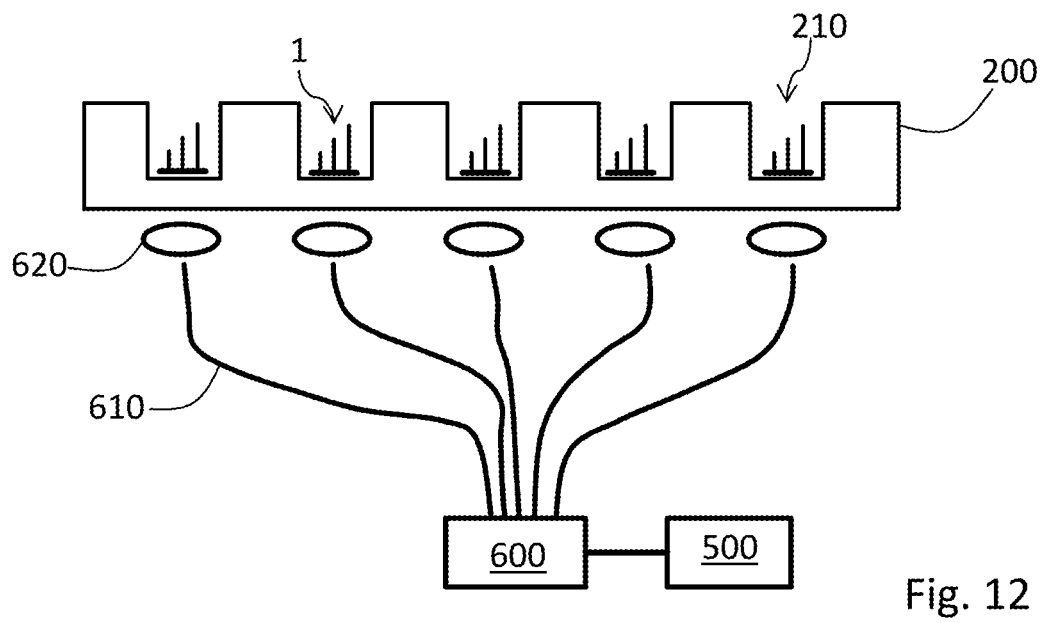
FIG. 12 shows a microtiter plate with several sensor devices according to the invention together with a plurality of light guides.

FIG. 12 schematically shows a transparent microtiter plate 200, in the wells 210 of which a respective sensor device 1 according to the invention has been inserted. Of the sensor device 1 the transparent carrier and three light guides are shown. Each well 210 of the microtiter plate 200 is assigned a light guide 610 and coupling optics 620. Coupling optics 620 is intended to direct light from the light guide 610 through the transparent microtiter plate 200 to the respective sensor device 1 according to the invention and to focus light corresponding to an optical response of the sensor elements of the sensor device into the respective light guide 610. All light guides are connected to a detector system 600. The detector system 600 detects the light guided in the individual light guides 610, which corresponds to an optical response of the sensor elements of the respective sensor device 1, and converts this into output signals which are evaluated by a control unit 500 in order to determine the concentration or partial pressure of at least one analyte. The evaluation is carried out separately for each sensor element of each sensor device 1. The detector system 600 also provides at least one light source to feed excitation light for the sensor elements of the sensor devices 1 into the light guides 610. In the embodiment shown, the control unit 500 also controls this at least one light source.

To perform its tasks, the control unit 500 has, for example, one or more microprocessors and memory units. The memory units contain program instructions for the execution of measurement protocols and evaluation procedures, as well as additional data required for this purpose, such as calibration data.

LIST OF REFERENCE SIGNS 1 sensor device
4 carrier
6 support (cell crown)
21, 22, 23, 24, 25 light guides
31, 32, 33 sensor element
41 retaining element
42 area (for interaction with positioning device)
100 sample container
101 wall (of the sample container)
110 distance (perpendicular from carrier)
150 sample
200 microtiter plate
210 well (of the microtiter plate)
211, 221, 231 first end (of the light guide)
212, 222, 232 second end (of the light guide)
300 camera
310 detector
400 ring light
410 excitation light
420 light (optical response)
500 control unit
600 detector system
610 light guide
620 coupling optics

What is claimed is:

1. A sensor device comprising:
   a plurality of light guides, each light guide having a first end and a second end;
   a plurality of sensor elements, wherein each sensor element of the plurality of sensor elements has an optical behavior dependent on at least one analyte, and wherein each sensor element of the plurality of sensor elements is disposed on the second end of a light guide of the plurality of light guides;
   a carrier on which the first end of each light guide of the plurality of light guides is arranged at a respective defined position, wherein
   the second end of each light guide of the plurality of light guides is positioned at a defined perpendicular distance to the carrier; and
   wherein the defined perpendicular distances of the second ends to the carrier for at least two light guides of the plurality of light guides are different.

2. The sensor device according to claim 1, wherein each light guide follows a predetermined path from its first end to its second end.

3. The sensor device according to claim 1, wherein more than one sensor element is arranged on the second end of at least one light guide of the plurality of light guides.

4. The sensor device according to claim 1, wherein a group of light guides of the plurality of light guides agree with respect to the sensor elements arranged at their respective second ends, and for each light guide of the group of light guides its respective second end is at a different perpendicular distance to the carrier.

5. The sensor device according to claim 1, wherein the carrier is formed from glass or a polymer.

6. The sensor device according to claim 1, wherein the light guides and the carrier are made of the same material and are connected to one another in a material-bonded manner.

7. The sensor device according to claim 1, wherein a support for a cell culture is provided on the carrier.

8. The sensor device according to claim 1, wherein one or more areas are formed on the carrier for interaction with a positioning device for the sensor device.

9. The sensor device according to claim 1, wherein the carrier is formed by at least one wall of a sample container.

10. A manufacturing method for a sensor device comprising a plurality of light guides, each light guide having a first end and a second end; a plurality of sensor elements, wherein each sensor element of the plurality of sensor elements has an optical behavior dependent on at least one analyte, and wherein each sensor element of the plurality of sensor elements is disposed on the second end of a light guide of the plurality of light guides; a carrier on which the first end of each light guide of the plurality of light guides is arranged at a respective defined position, wherein the second end of each light guide of the plurality of light guides is positioned at a defined perpendicular distance to the carrier; and wherein the defined perpendicular distances of the second ends to the carrier for at least two light guides of the plurality of light guides are different;

the method comprising forming the light guides by 3D printing and/or by material removal by means of laser radiation and/or by material restructuring by means of laser radiation.

11. The manufacturing method according to claim 10, further comprising forming the carrier by 3D printing.

12. A method for measuring at least one analyte in a sample, the method comprising at least the steps:

placing at least one sensor device in a sample container, the at least one sensor device comprising a plurality of light guides, each light guide having a first end and a second end; a plurality of sensor elements, wherein each sensor element of the plurality of sensor elements has an optical behavior dependent on at least one analyte, and wherein each sensor element of the plurality of sensor elements is disposed on the second end of a light guide of the plurality of light guides; a carrier on which the first end of each light guide of the plurality of light guides is arranged at a respective defined position, wherein the second end of each light guide of the plurality of light guides is positioned at a defined perpendicular distance to the carrier; and wherein the defined perpendicular distances of the second ends to the carrier for at least two light guides of the plurality of light guides are different;

coupling excitation light into at least a subset of the light guides of the sensor device, wherein the excitation light is suitable to excite the optical behavior of at least one sensor element arranged at the second end of a light guide of the subset of the light guides;

detecting with at least one detector the light guided through the subset of the light guides, which light corresponds to the response of the at least one sensor element corresponding to the excited optical behavior; and evaluating an output signal of the at least one detector to measure the at least one analyte.

13. The method according to claim 12, wherein the sample container is a microtiter plate and a respective sensor device is placed in each of a plurality of wells of the microtiter plate.

14. A method for measuring at least one analyte in a sample, the method comprising at least the steps:

filling a sample container with the sample, at least one wall of the sample container forming a carrier of a sensor device, the sensor device comprising a plurality of light guides, each light guide having a first end and a second end; a plurality of sensor elements, wherein each sensor element of the plurality of sensor elements has an optical behavior dependent on at least one analyte, and wherein each sensor element of the plurality of sensor elements is disposed on the second end of a light guide of the plurality of light guides; the carrier on which the first end of each light guide of the plurality of light guides is arranged at a respective defined position, wherein the second end of each light guide of the plurality of light guides is positioned at a defined perpendicular distance to the carrier; and wherein the defined perpendicular distances of the second ends to the carrier for at least two light guides of the plurality of light guides are different;

coupling excitation light into at least a subset of the light guides of the sensor device, wherein the excitation light is suitable to excite the optical behavior of at least one sensor element disposed at the second end of a light guide of the subset of the light guides;

detecting with at least one detector the light guided through the subset of the light guides, which light corresponds to the response of the at least one sensor element corresponding to the excited optical behavior; and evaluating an output signal of the at least one detector to measure the at least one analyte.

* * * * *